United States Patent [19]

Auth

[11] Patent Number: 4,829,999
[45] Date of Patent: May 16, 1989

[54] SIDE MOUNT GUIDEWIRE GRIPPING DEVICE

[75] Inventor: David C. Auth, Redmond, Wash.

[73] Assignee: E. R. Squibb and Sons, Inc., Princeton, N.J.

[21] Appl. No.: 74,808

[22] Filed: Jul. 17, 1987

[51] Int. Cl.$^4$ ............................................. A61B 19/00
[52] U.S. Cl. ............................... 128/303 R; 24/115 R; 81/177.3; 81/487
[58] Field of Search .................... 24/115 R, 120–122, 24/115 G, 129 R, 129 C, 130, 131 R, 132 R, 530, 537, 538, 539, 545, 556, 558, 570, 571; 81/177.3, 487; 128/303 R, 344, 346, 354; 140/93 R, 123.5; 269/254 R

[56] References Cited

U.S. PATENT DOCUMENTS

| | | | |
|---|---|---|---|
| 1,111,878 | 9/1914 | Carroll | 81/487 X |
| 1,133,388 | 3/1915 | Merrill | 24/530 X |
| 1,410,415 | 2/1922 | Shell | 81/487 X |
| 2,009,825 | 7/1935 | Wappler | 604/171 |
| 2,025,848 | 12/1935 | Collis | 24/570 X |
| 2,621,664 | 12/1952 | Leclabart | 24/530 X |
| 3,043,902 | 7/1962 | Klein | 24/129 R |
| 3,312,128 | 4/1967 | Wasson | 81/487 |
| 3,388,227 | 6/1988 | Basso et al. | 24/129 R |
| 3,537,451 | 11/1970 | Beck et al. | 604/165 |
| 4,598,708 | 7/1986 | Beranek | 81/487 X |
| 4,726,369 | 2/1988 | Mar | 128/303 R |

Primary Examiner—Dalton L. Truluck
Attorney, Agent, or Firm—Lawrence S. Levinson; Robert E. Lee, Jr.

[57] ABSTRACT

The guidewire gripping device is usable in connection with guidewires of the type used in medical application, i.e., for guiding catheters. The guidewire gripping device is constructed from a spring loaded, slitted cylindrical body.

6 Claims, 1 Drawing Sheet

SIDE MOUNT GUIDEWIRE GRIPPING DEVICE

BACKGROUND OF THE INVENTION

The present invention relates to a device which may be attached to a wire in order to permit one to turn the wire comfortably. In particular, the device relates to a guidewire gripping device.

Modern angiographic practice calls for the extensive use of guidewires during the catheterization of human arteries and arterial branches. A typical steerable guide wire consists of a flexible distal section, usually a spring, connected to along slender section of wire or tubing which is manipulated for axial advancement and retraction, and rotational torque transmission. This combination of features allows the guidewire to negotiate through the compound curves involved in the human arterial system, and when finally in place, to act as a guide for flexible diagnostic and therapeutic catheters which are slipped over it.

Since the proximal ends of the guidewires are typically small diameter wire or tubing (often hard-drawn stainless steel) and have a hard, polished, surface, they are very difficult to grasp securely. Medical device manufacturers currently provide a variety of so-called "guidewire gripping devices", or "torquers", or "handles" which are intended to grip and manipulate the wires, but they all suffer from one or more deficiencies.

SUMMARY OF THE INVENTION

The present invention is a guidewire gripping device which may be attached to a medical guidewire. The guidewire gripping device comprises an elongated, cylindrical body made of an elastic material. The body includes an elongated slot which extends into the body from its circumference. The slot is adapted to receive a guidewire. The device also includes handles attached to either side of the elongated slot. Force applied to the handles causes the slot to open for insertion of the guidewire. The internal sides of the slot act to frictionally grip the guidewire.

DETAILED DESCRIPTION OF THE PREFERRED EMBODIMENT

Figure 1:
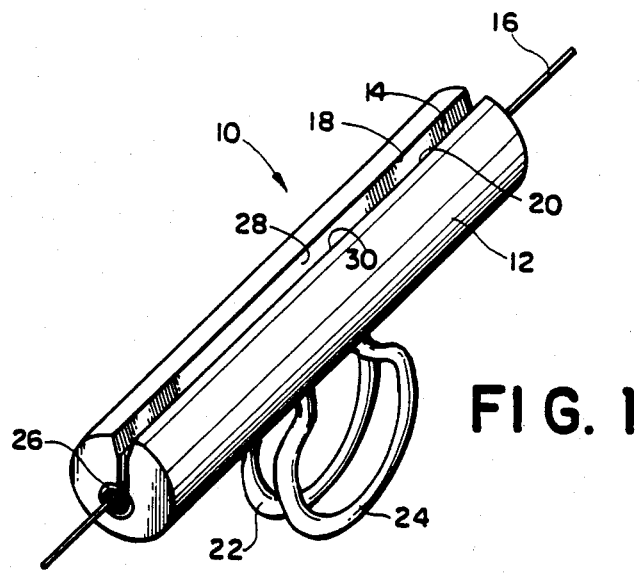
FIG. 1 is a perspective view of the guidewire gripping device the present invention.
Figures 2, 3:
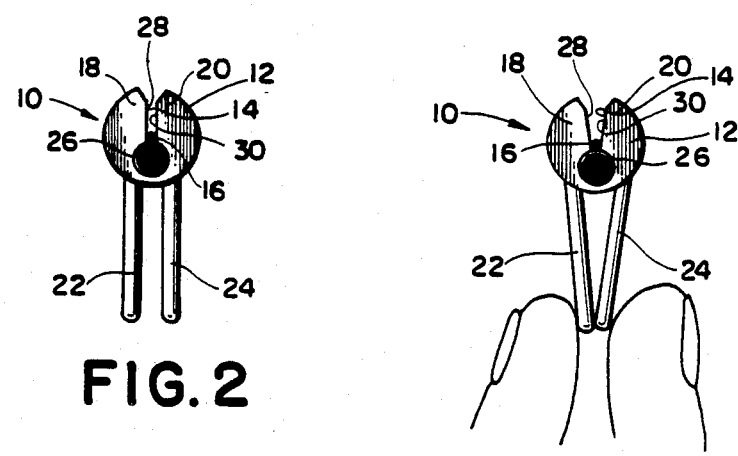
FIG. 2 is a side view of the device of the present invention in use.
FIG. 3 is a side view illustrating the manner in which the device is mounted onto a guidewire.

FIG. 1 depicts the preferred embodiment of the guidewire gripping device 10 of the present invention. The guidewire gripping device 10 is comprised of body 12 about 1.25" long and ⅜" diameter which includes a slot 14 to permit sidewise insertion of a guidewire 16. It simultaneously provides jaws 18, 20 for gripping and springiness for jaw-bite force. The jaws 18, 20 can be opened against the spring force and installed onto the guidewire 16 with one hand as shown in FIG. 3. The wire size capacity is variable depending upon the amount of compression of the handles 22, 24. A stop 26 is located adjacent to the centerline of the guidewire gripping device, so that the guidewire 16 will automatically locate near the rotational center.

To provide more grip, gritty material can be deposited on the grip faces 28, 30 directly, or onto substrates which are subsequently bonded to the jaws 18, 20. If grit material is used, it should be sufficiently fine so as not to cause excessive scratch damage to the guidewire 16 in normal use.

The cylindrical body 12 is made from a material which can be molded or easily shaped, while at the same time having a large yield strain capacity, so that it can accommodate varying wire sizes without losing its springiness. Handles 22, 24 are provided for separating the jaws 18, 20 and in some configurations may be removable so that the system can be inserted into a larger member for machine driven rotation of the guidewire 16, such as might be desired for guidewire mediated thrombectomy or for orthogonally displacing the guidewire friction vector from the longitudinal direction to the circumferential direction.

The ⅜" diameter of the preferred embodiment provides for adequate elastic energy storage without yield and yet, enables easy twirling between the thumb and finger. Fabricated from aluminum alloy or plastic (such as for example, Ultem®), the device 10 is light in weight, potentially inexpensive to manufacture, and sterilizable. It can be relocated with ease to a different place on the guidewire 16 with one hand and is thus "inchable." Lightness of weight is an advantage in that it reduces the likelihood of undesirable kinking of the guidewire. Clearly this configuration is eminently side-loadable, and is able to accommodate a diverse range of guidewire diameters, i.e., from about 0.004" to about 0.018".

I claim:

1. A guidewire gripping device which may be attached to a medical guidewire comprising:
   (a) an elongated, cylindrical body comprised of an elastic material having an elongated slot which extends to the circumference thereof and is adapted to receive a guidewire, said slot being biased to grip a guidewire placed therein by the elastic nature of said cylindrical body; and
   (b) handle means attached to and extending from said elongated, cylindrical body on either side of said elongated slot for application of force to said device to cause said slot to open for insertion of said guidewire, the internal sides of said slot acting to frictionally grip said guidewire, said slot operable to grip said guidewire having a diameter falling within the range of 0.009 inches to 0.018 inches.

2. The device of claim 1 wherein a gritted material is attached to the internal faces of said slot to increase frictional grip on said guidewire.

3. The device of claim 1 wherein teeth are formed on the internal surfaces of said slot to increase the frictional grip on said guidewire.

4. The device of claim 1 further comprising stop near the center for aiding central location of the guidewire during insertion and inching.

5. The device of claim 1 including an integral jaw and spring structure.

6. The device of claim 1 wherein said range includes 0.004 inches.

* * * * *

UNITED STATES PATENT AND TRADEMARK OFFICE
CERTIFICATE OF CORRECTION

PATENT NO. : 4,829,999
DATED : May 16, 1989
INVENTOR(S) : DAVID C. AUTH

It is certified that error appears in the above-identified patent and that said Letters Patent is hereby corrected as shown below:

Column 1, line 57, "3/8"" should read -- 1/4" --.

Column 2, line 21, "3/8"" should read -- 1/4" --.

Column 2, line 51, Claim 1, "0.009 inches" should read -- 0.004 inches --.

Column 2, lines 63-64, Claim 6, "includes 0.004 inches" should read -- is from 0.009 inches to 0.018 inches --.

Signed and Sealed this

Thirty-first Day of July, 1990

Attest:

HARRY F. MANBECK, JR.

*Attesting Officer*  *Commissioner of Patents and Trademarks*